United States Patent [19]
Zutter

[11] Patent Number: 5,453,547
[45] Date of Patent: Sep. 26, 1995

[54] PROCESS FOR THE MANUFACTURE OF GAMMA-ACETOXYTIGLIC ALDEHYDE

[75] Inventor: Ulriche Zutter, Basel, Switzerland

[73] Assignee: Hoffman-La Roche Inc., Nutley, N.J.

[21] Appl. No.: 316,654

[22] Filed: Sep. 30, 1994

[30] Foreign Application Priority Data

Oct. 13, 1993 [CH] Switzerland ............................ 3077/93

[51] Int. Cl.⁶ .......................... C07C 45/40; C07C 45/28; C07C 45/27
[52] U.S. Cl. .......................... 568/469; 568/448; 568/449; 568/467; 568/496
[58] Field of Search ...................................... 568/469, 467, 568/449, 496, 448

[56] References Cited

U.S. PATENT DOCUMENTS 3,639,437  2/1972  Fischer et al. ............................ 568/469

FOREIGN PATENT DOCUMENTS

| 564339  | 1/1958  | European Pat. Off. . |
| 1576842 | 6/1969  | European Pat. Off. . |
| 2266689 | 4/1975  | European Pat. Off. . |
| 2383908 | 3/1978  | European Pat. Off. . |
| 2513999 | 10/1970 | Germany ............................ 568/469 |
| 0825492 | 4/1981  | U.S.S.R. ............................ 568/469 |
| 1172969 | 12/1969 | United Kingdom .................. 568/469 |

OTHER PUBLICATIONS

Geraghty and Morris, Papers, pp. 603–607 Aug. 1989.
Stevens, et al., Jo. of the Amer. Chem. Society, 108, 1039–1049 1986.
FR 2 383 908 Abstract for Document B1 1978.
FR 2 266 689 Abstract for Document B2 1975.

Primary Examiner—Werren B. Lone
Attorney, Agent, or Firm—George M. Gould; William H. Epstein; Bruce A. Pokras

[57] ABSTRACT

A novel process for the manufacture of γ-acetoxytiglic aldehyde ("$C_5$-aldehyde"), which is known as an important starting material for the production of vitamin A acetate from a (β-ionylidenethyl)triphenylphosphonium halide and $C_5$-aldehyde, comprises treating a pentenyn-3-ol of the formula $HC\equiv C-C(CH_3)(OH)-CH=C(R)_2$ (II), wherein both R's signify either hydrogen or methyl, with ozone, preferably in a lower alkanol $R^1OH$, wherein $R^1$ signifies $C_{1-4}$-alkyl, to obtain an aldehyde 2-hydroxy-2-methyl-3-butynal of the formula $HC\equiv C-C(CH_3)(OH)-CHO$ (III). The aldehyde III may be converted to the $C_5$-aldehyde by conventional means.

5 Claims, No Drawings

PROCESS FOR THE MANUFACTURE OF GAMMA-ACETOXYTIGLIC ALDEHYDE

SUMMARY OF THE INVENTION

The present invention is concerned with a novel process for the manufacture of γ-acetoxytiglic aldehyde ("$C_5$-aldehyde") which has the formula:

$$CH_3COO-CH_2CH=C(CH_3)-CHO \qquad I$$

and which is known as a starting material for the manufacture of vitamin A acetate from a (β-ionylidenethyl)triphenylphosphonium halide ("$C_{15}$-vinyl salt") and $C_5$-aldehyde.

In the final step of the known vitamin A acetate synthesis, the $C_5$-aldehyde is coupled with the $C_{15}$-vinyl salt by means of a Wittig reaction. This gives directly with high selectivity all-trans-vitamin A acetate which is preferred because of its particularly pronounced biological activity. However, the present means for producing the $C_5$-aldehyde is still found to be complicated and too expensive.

The manufacture of $C_5$-aldehyde, by catalytically hydrogenating 2-hydroxy-2-methyl-3-butynal of the formula:

$$HC\equiv C-C(CH_3)(OH)-CHO \qquad III$$

to the known 2-hydroxy-2-methyl-3-butenal of the formula $$H_2C=CH-C(CH_3)(OH)-CHO \qquad V$$

and converting the compound of formula V in a manner known per se into the desired $C_5$-aldehyde, is well known.

However, it has been discovered that the starting aldehyde of formula III used in the above process may be obtained by a process which comprises subjecting a pentenyn-3-ol of the formula:

$$HC\equiv C-C(CH_3)(OH)-CH=C(R)_2 \qquad II$$

wherein both R's are either hydrogen or methyl, to a selective ozonolysis. The ozonolysis of the pentenyn-3-ol may be carried out by any conventional means in the art. Preferably, the ozonolysis of the pentenyn-3-ol is carried out while it is dissolved in a lower alkanol, $R^1OH$, wherein $R^1$ is $C_{1-4}$-alkyl, preferably methyl or ethyl, especially methyl. It is particularly preferred that the ozonolysis be carried out at a temperature from about −20° C. to about 0° C.

DETAILED DESCRIPTION OF THE INVENTION

The process of the invention comprises the manufacture of an aldehyde of the formula:

$$HC\equiv C-C(CH_3)(OH)-CHO \qquad III$$

from a pentenyn-3-ol of the formula:

$$HC\equiv C(C-C(CH_3)(OH)-CH=C(R)_2 \qquad II$$

wherein R is hydrogen or methyl, comprising treating said pentenyn-3-ol with ozone. Preferably, the pentenyn-3-ol is in solution during said treatment. The solution preferably contains said pentenyn-3-ol and a lower alkanol, $R^1OH$, wherein $R^1$ is $C_{1-4}$-alkyl, preferably methyl or ethyl, especially methyl. The treatment is preferably carried out at a temperature of from about −20° C. to about 0° C.

The compounds of formula II i.e., encompassing the compounds of formulas:

$$HC\equiv C-C(CH_3)(OH)-CH=CH_2$$

and $$HC\equiv C-C(CH_3)(OH)-CH=C(CH_3)_2$$

are known compounds, but their treatment with ozone is not described in the prior art.

The ozonolysis of the invention is preferably effected in a lower alkanol, $R^1OH$, preferably methanol or ethanol, especially in methanol, as the solvent and at relatively low temperatures up to about 0° C/, preferably at temperatures in the range of about −20° C. to about 0° C. The ozone is conducted into the reaction solution, which is held at the low temperature, until a complete or almost complete conversion has been determined, e.g., by gas chromatography. Moreover, it is recommended, after completion of the ozonolysis, to gas the ozonolysis solution with an inert gas, e.g., argon, in order to remove excess ozone. When a lower alkanol $R^1OH$ is used as a solvent a 1-alkoxyalkylhydroperoxide of the formula:

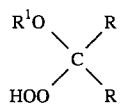

$$\qquad IV$$

wherein both R's are hydrogen or methyl and $R^1$ is $C_{1-4}$-alkyl, may be obtained as a byproduct. Moreover, when the lower alkanol is used as the solvent in the ozonolysis, it is possible for the 2-hydroxy-2-methyl-3-butynal to be converted partly into the corresponding hemiacetal of the formula:

$$HC\equiv C-C(CH_3)(OH)-CH(OH)(OR^1).$$

The above hydrogenation of formula III to formula V may be performed without the necessity of firstly removing one or both of the byproducts, 1-alkoxyalkyl-hydroperoxide and the hemiacetal. The hydrogenation is selective in the case of the 2-hydroxy-2-methyl-3butynal of formula III.

The subsequent hydrogenation of the 2-hydroxy-2-methyl-3-butynal and of hemiacetal which may be present, in which the (respective) triple bond is reduced selectively to a double bond, as well as the simultaneous hydrogenolytic cleavage of the 1-alkoxyalkyl-hydroperoxide, is conveniently effected by the addition of the still cold ozonolysis solution to the catalyst in suspension while introducing hydrogen. A platinum or palladium catalyst is an especially suitable catalyst. A palladium catalyst, e.g., palladium on aluminium oxide or palladium on charcoal, has a greater selectivity than a platinum catalyst and is therefore preferred. The catalyst is preferably pre-hydrogenated in the corresponding alkanol $R^1OH$, e.g., methanol, at room temperature. There is thus obtained the catalyst suspension to which is subsequently added the cold ozonolysis solution. This addition is preferably carried out dropwise: in this manner the otherwise frequently observed hydroperoxide-attributed poisoning of the catalyst is avoided. Moreover, the rate of addition during the hydrogenation is controlled in such a manner that the peroxide concentration remains as low as possible. Likewise, care must be taken that during the hydrogenation the butynal never reacts completely, since otherwise over-hydrogenated product, namely 2-hydroxy-2-methyl-butanal, also results. This is achieved by hydrogenating the individual portions of the ozonolysis solution up to a residual butynal content. The hydrogenation is conveniently effected at normal pressure or an over-pressure of up to about 20 bar and at temperatures between about 20° C. and about 40° C., preferably at room temperature.

After the hydrogen uptake has finished, the catalyst is removed, e.g., by filtration. The isolation of the thus-produced 2-hydroxy-2-methyl-3-butenal has been found to be unnecessary, since its alcohol solution can be treated immediately in the next process step. The same also applies to a hemiacetal of this compound which may be present and which has been obtained by catalytic, selective hydrogenation of the butynal hemiacetal resulting in the ozonolysis.

Reaction conditions for the known selective hydrogenation of 2-hydroxy-2-methyl-3-butynal of formula III to the corresponding 3-butenal of formula V are also described in Belgian Patent Specification 64,339. In this case, however, the butynal of formula III is in turn obtained by ethynylation (reaction with acetylene) of methylglyoxal acetal.

As mentioned above, the 2-hydroxy-2-methyl-3-butenal of formula V obtained in the second process step can be converted in a manner known per se into the desired $C_5$-aldehyde of formula I. This conversion is conveniently effected by acetalizing the butenal [as well as any hemiacetal thereof of the formula $H_2C=CH-C(CH_3)(OH)-CH(OH)(OR^1)$ which may be present] to the corresponding dialkyl acetal of the formula

$$H_2C=CH-C(CH_3)(OH)-CH(OR^2)_2 \qquad VI$$

wherein $R^2$ signifies $C_{1-4}$-alkyl, [or fully to the dialkyl acetal of the formula $H_2C=CH-C(CH_3)(OH)-CH(OR^1)(OR^2)$ VI'], acetylating the dialkyl acetal, subjecting the resulting 2-acetoxy-2-methyl-3-butenal dialkyl acetal of the formula:

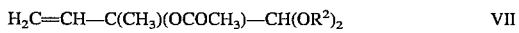

$$H_2C=CH-C(CH_3)(OCOCH_3)-CH(OR^2)_2 \qquad VII$$

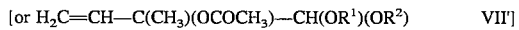

[or $H_2C=CH-C(CH_3)(OCOCH_3)-CH(OR^1)(OR^2)$ VII']

to a catalytic rearrangement to the γ-acetoxytiglic aldehyde dialkyl acetal of the formula:

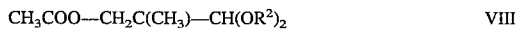

$$CH_3COO-CH_2C(CH_3)=CH(OR^2)_2 \qquad VIII$$

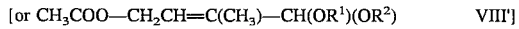

[or $CH_3COO-CH_2CH=C(CH_3)-CH(OR^1)(OR^2)$ VIII']

and converting this by acid-catalyzed hydrolysis into the desired $C_5$-aldehyde of formula I.

The acetalization is preferably carried out using acetone dimethyl acetal as the acetalizing agent, conveniently in an about 1 molar excess based on the amount of pentenyn-3-ol of formula II which is used. Moreover, the reaction is effected in the presence of an acid, preferably hydrochloric acid or sulphuric acid, and, as mentioned above, using the alcoholic product solution of the previous step. The acetalization is conveniently effected at an elevated temperature, preferably at the reflux temperature of the reaction mixture. The product, 2-hydroxy-2-methyl-3-butenal dimethyl acetal, can be isolated and purified in a manner known per se, for example by neutralization of the mixture with a base, e.g., sodium methylate, distilling off the solvent and finally distillation of the residue under reduced pressure.

The acetalization can also be carried out by a known acid-catalyzed reaction of the butenal and any hemiacetal with the corresponding lower alkanol $R^2OH$ (wherein $R^2$ is $C_{1-4}$-alkyl), with hydrochloric acid being the preferred acid catalyst.

The subsequent acetylation can also be effected in a manner known per se, for example using a corresponding acetyl halide, especially the chloride, or acetic anhydride. The acetylation is preferably carried out using an excess of boiling acetic anhydride, the acetic acid formed being distilled off continuously and rapidly from the reaction mixture. In this manner the acetylation proceeds almost quantitatively. Depending on the apparatus, an excess of acid anhydride, especially about 2 to about 10 mol of acid anhydride per mol of dialkyl acetal VI (and VI'), is conveniently used. After the reaction the acetylated product can be isolated from the reaction mixture in a conventional manner and can also be purified by conventional means.

The next process step, the catalytic rearrangement of the 2-acetoxy-2-methyl-3-butenal dialkyl acetal of formula VII (and possibly also VII'), can be carried out by conventional means, for example, according to the methods described and exemplified in DOS 1,297,597 or in DOS 2,840,125, namely by heating the dialkyl acetal VII or VII' in the presence of metallic copper or a copper compound, especially copper(I) chloride, as the catalyst at temperatures of 50° to 250° C., preferably 110° to 180° C. The copper(I) chloride can be used alone or held on an inert carrier material and is generally used in amounts of 0.005 to 5 weight percent, preferably 0.05 to 0.5 weight percent, calculated as copper based on the starting material. The low-boiling byproducts which result during the rearrangement can be separated from the reaction mixture by distillation, preferably continuously, at normal pressure or reduced pressure, preferably at a pressure of 100 to 500 mbar, more preferably at 200 to 350 mbar, or alternatively by stripping with an inert gas, e.g., nitrogen or argon, or even carbon dioxide, methane, hydrogen or methyl chloride, flowing through the reaction mixture.

The method described and exemplified in DOS 2,513,198 can be used as an alternative to the above rearrangement procedure. In this method the rearrangement is effected in the presence of a palladium catalyst of the formula:

$$(PdX_2Y)_n$$

wherein n signifies 1 or 2 and X signifies chlorine or bromine and, where n is 1, Y signifies the group $(R^3CN)_2$, wherein $R^3$ represents an alkyl or aryl group, or, where n is 2, Y signifies a mono-olefinically unsaturated aliphatic or cycloaliphatic hydrocarbon residue.

The catalyst is preferably bis-(acetonitrile)-palladium chloride or -palladium bromide of the formula $PdX_2(CH_3CN)_2$, especially the former, i.e., of the formula $PdCl_2(CH_3CN)_2$. The rearrangement can be carried out in the presence or absence of a solvent, with chlorinated hydrocarbons, such as chlorinated ethylenes, e.g., di-, tri- and tetrachloroethylene; lower aliphatic ketones, e.g. acetone; lower aliphatic or cyclic ethers, e.g. diisopropyl ether or dioxan; as well as lower aliphatic esters, e.g., ethyl acetate, especially coming into consideration as the solvents. Moreover, the rearrangement is preferably effected in a temperature range between about room temperature and about 100° C., especially between about 30° and about 50° C. The amount of catalyst can vary from less than 1 part per thousand by weight to about 7–8 parts per thousand by weight based on the amount of starting material used. The reaction time lies between a few minutes and a number of hours, e.g., about 20 hours, depending on the reaction temperature and amount of catalyst used.

In general, the DOS 2,513,198 method [use of a palladium catalyst $(PdX_2Y)_n$] is preferred to that of DOS 1,297,597 or DOS 2,840,125 [use of metallic copper or a copper compound, especially copper(I) chloride]. In each case the isolation of the rearrangement product and its purification can be effected according to methods known per se.

The final step to the desired $C_5$-aldehyde can be effected by acidic hydrolysis of the product of the previous step in a manner known per se, for example by treating the γ-acetoxytiglic aldehyde dialkyl acetal (VIII) with a dilute mineral acid, e.g., hydrochloric acid, conveniently at room temperature. In this case too, the product can be isolated and purified in a manner known per se.

The invention is illustrated by the following Examples.

EXAMPLE 1

Production of 3,5-dimethyl-4-hexen-1-yn-3-ol (Starting Material for the Ozonolysis)

1.875 l of ammonia are placed in a 4.5 l sulphonation flask fitted with a stirrer, gas inlet tube, thermometer and carbon dioxide/acetone condenser at an internal temperature of about −34° C. while cooling with a carbon dioxide/acetone bath at −40° C. Subsequently, 26.03 g (3.75 mol) of lithium wire in 2–3 cm long pieces are added within 45 minutes while stirring and the resulting dark-blue solution is stirred for 15 minutes. Acetylene is then introduced at a throughput velocity of 4 l/min. through the gas inlet tube into the ammonia solution at an internal temperature of −34° C. (bath temperature −42° to −44° C.). Once, after 45 minutes, a colour change from dark-blue to grey (transparent) has taken place, further acetylene is introduced in the following 30 minutes, following which the acetylene consumption amounts to about 300 l. The internal temperature thereby drops to −37° C. at a bath temperature of −35° C.

The acetone in the condenser is now warmed from −78° C. to −20° C. and the carbon dioxide/acetone bath is replaced by a water bath at 30°–40° C. While in this manner the ammonia is distilling off, the volume of the reaction mixture is held constant by the continuous dropwise addition of a total of about 1.875 l of diethyl ether. Thereby, the internal temperature increases from −37° C. to +5° C. and a white suspension forms from the grey reaction mixture. The reaction mixture is held at 5° C. for 15 minutes and is then saturated with 2 l/min. of acetylene for 30 minutes without a water bath. The mixture is now cooled to −10° C. with the continued introduction of acetylene (2 l/min.) and at this temperature a solution of 294.5 g (3 mol) of mesityl oxide in 255 ml of diethyl ether is added dropwise within 50 minutes at a bath temperature of about −30° C. Subsequently, the mixture is stirred for 10 minutes and the acetylene introduction is stopped, since the conversion is then complete according to gas chromatography (GC).

For the neutralization, about 870 ml of 30% sulphuric acid at −5° to +5° C. are then slowly added dropwise within 3 hours and while stirring intensively and while holding the bath temperature at −30° C. until the reaction mixture has a pH of 7. Then the aqueous phase is separated off in a separating funnel. The organic phase is dried over anhydrous sodium sulphate (100 g) and, after filtering off the drying agent, the solvent is evaporated off under reduced pressure at 30° C. The residue (364.3 g, 97.8% of the theoretical yield) is subjected to a fractional distillation: the relevant details are compiled in the following table.

| Crude product component | Bath temperature, °C. | B.p., °C. | Pressure, mbar | Weight | Purity according to GC |
| --- | --- | --- | --- | --- | --- |
| Fore-run | 65–70° | 46–65° | 23 | 6.5 g | 92.4 area % |
| Main | 74–80° | 66–69° | 20 | 332.2 g | 98.6 area % |
| fraction Residue | | | | 16.1 g | 70.7 area % |

The main fraction gives 332.2 g (89.2% of the theoretical yield) of pale yellow liquid, b.p. 66°–690/20 mbar, which consists to 98.6 area % of the desired 3,5-dimethyl-4-hexen-1-yn-3-ol according to gas chromatography.

EXAMPLE 2

Production of 2-hydroxy-2-methyl-3-butynal (Formula III)

Ozone is conducted for 5 hours while stirring through a solution of 49.7 g (400 mol) of 3,5-dimethyl-4-hexen-1-yn-3-ol (GC 98.6 area %; produced according to Example 1) in 200 ml of methanol at −20° C. in a 350 ml cooling jacketed flask fitted with a stirrer, thermometer, gas inlet tube and bubble counter. During the passage of ozone, excess ozone is vented via the bubble counter. Complete conversion takes place within this period according to gas chromatography. In order to remove the excess ozone, the ozonolysis solution is gassed with argon at −20° C. for 30 minutes. This solution is subsequently transferred into a 250 ml cooling dropping funnel (cooled to −20° C.) and diluted to 250 ml with a small amount of methanol rinsings. According to gas chromatography the reaction product, which is dissolved in the methanol, consists mainly of the desired 2-hydroxy-2-methyl-3-butynal. 1-Methoxy-1-methylethylhydroperoxide is identified as a byproduct.

EXAMPLE 3

Production of 2-hydroxy-2-methyl-3-butenal (Formula V)

10 g of 5% palladium on aluminium oxide in 800 ml of methanol are pre-hydrogenated at room temperature for 20 minutes in a 1.5 l sulphonation flask fitted with a graduated 250 ml cooling dropping funnel (with pressure balance), gasification stirrer, thermometer and septum (for sample withdrawal). Then, 25 ml of ozonolysis solution (see Example 2) are added dropwise to the catalyst suspension and the mixture is subsequently hydrogenated at normal pressure until 1.4 l of hydrogen have been taken up. A minimum 2–20% residual 2-hydroxy-2-methyl-3-butynal content is guaranteed with the aid of gas chromatographical analysis in order to avoid the formation of over-hydrogenated product. The remaining ozonolysis solution is added in nine 25 ml portions and in each case the mixture is hydrogenated at about 30° C. (to which temperature the reaction mixture warms spontaneously) until 1.7 l of hydrogen have been taken up. As previously, the minimum 2–20% residual 2-hydroxy-2-methyl-3-butynal content is guaranteed. The hydrogenation time of the 25 ml portions increases from 10 minutes for the 1st portion to 50 minutes for the 10th portion, which gives a total hydrogenation time of 6 hours. After a total hydrogen uptake of 16.8 l (theory 19.3 l; no butynal and less than 0.5% over-hydrogenation can be detected by GC analysis) the catalyst is filtered off over about 20 g of Dicalite Speedex (filter aid) and washed with 100 ml of methanol. The filtrate (about 1.2 l) contains the desired 2-hydroxy-2-methyl-3-butenal, which is not contaminated by any peroxide according to iodometric titration of a 1 ml sample.

EXAMPLE 4

Production of 2-hydroxy-2-methyl-3-butenal dimethyl acetal (Formula VI)

The filtrate of the last process step (about 1.2 l; see Example 3) is treated with 83.3 g (800 mmol, 98 ml) of acetone dimethyl acetal in a 1.5 l sulphonation flask fitted with a stirrer, thermometer and reflux condenser. Subsequently, the pH is adjusted from about 4.5 to about 1 with 1.0 ml of 37% hydrochloric acid and the reaction mixture is heated to reflux temperature at a bath temperature of 85° C. for 2.5 hours. Thereafter, the mixture is cooled to room temperature and the pH is adjusted to 7–8 with about 2.5 ml of 30% sodium methylate in methanol. The solvent (methanol with a small amount of acetone) is distilled off over a 50 cm packed column (Θ 2.5 cm) filled with Wilson coils at normal pressure, a head temperature of 62°–65° C. and an oil bath temperature of 90°–95° C. and the residue (81 g) is subjected to a fractional distillation under reduced pressure (water-jet vacuum) over a silver-coated 10 cm packed column Θ 1.5 cm) filled with Wilson coils. The following fractions are withdrawn:

| Fraction | Bath temperature °C. | B.p., °C. | Pressure mbar | Weight | GC area % product |
| --- | --- | --- | --- | --- | --- |
| 1 | 55° | 42–27° | $10^3$–60 | 24.6 g | 0.0 |
| 2 | 55–72° | 25–62° | 19 | 1.4 g | 73.6 |
| 3 | 69–135° | 63–65° | 19 | 41.4 g | 97.0 |
| Residue | | | | 9.4 g | |

The main fraction (3) gives 41.4 g (70.8% of the theoretical yield) of colourless liquid, b.p. 63°–65° C./19 mbar, which consists to 97.0 area % of the desired product 2-hydroxy-2-methyl-3-butenal dimethyl acetal according to gas chromatography.

EXAMPLE 5

Production of 2-Hydroxy-2-methyl-3-butynal (Formula III)

Ozone is conducted for 5.5 hours while stirring through a solution of 38.45 g (400 mmol) of 3-hydroxy-3-methyl-1-penten-4-yne (GC 98.0 area %) in 200 ml of methanol at −20° C. in a 350 ml cooling-jacketed flask fitted with a stirrer, thermometer, gas inlet tube and bubble counter. During the passage of ozone, excess ozone is vented via the bubble counter. Practically complete conversion takes place within this period according to gas chomatography. In order to remove the excess ozone, the ozonolysis solution is gassed with argon at −20° C. for 30 minutes. This solution is subsequently transferred into a 250 ml cooling dropping funnel (cooled to −20° C.) and diluted to 225 ml with a small amount of methanol rinsings. According to gas chromatography the reaction product, which is dissolved in the methanol, consists mainly of the desired 2-hydroxy-2-methyl-3butynal. Methoxymethyl-hydroperoxide is identified as a byproduct.

EXAMPLE 6

Production of 2-hydroxy-2-methyl-3-butenal (Formula V)

7.7 g of 5% palladium on aluminium oxide in 800 ml of methanol are pre-hydrogenated for 20 minutes at room temperature in a 1.5 l sulphonation flask fitted with a graduated 250 ml cooling dropping funnel (with pressure balance), gasification stirrer, thermometer and septum (for sample withdrawal). Then, 25 ml of ozonolysis solution (see Example 5) are added dropwise to the catalyst suspension and the mixture is subsequently hydrogenated at normal pressure until 1.4 l of hydrogen have been taken up. A minimum 2–20% residual 2-hydroxy-2-methyl-3-butynal content is guaranteed with the aid of gas chromatographical analysis in order to avoid the formation of over-hydrogenated product. The remaining ozonolysis solution is added in nine 25 ml portions and in each case hydrogenated at about 30° C. (to which temperature the reaction mixture warms spontaneously) until 1.5 l of hydrogen have been taken up. As earlier, the minimum 2–20% residual 2-hydroxy-2-methyl-3-butynal content is guaranteed. The hydrogenation period of the 25 ml portions increases from 15 to 25 minutes, which gives a total hydrogenation time of 3.5 hours. After a total hydrogen uptake of 13.5 l (theory 19.3 l; no butynal and only about 1.5% over-hydrogenation can be detected by GC analysis) the catalyst is filtered off over about 20 g of Dicalite Speedex (filter aid) and washed with 100 ml of methanol. The filtrate (about 1.2 l) contains the desired 2-hydroxy-2-methyl-3-butenal, which is not contaminated with peroxide according to iodometric titration of a 1 ml sample.

EXAMPLE 7

Production of 2-hydroxy-2-methyl-3-butenal dimethyl acetal (Formula VI)

The filtrate of the last process step (about 1.2 l; see Example 6) is treated with 125 g (1200 mmol, 147.2 ml) of acetone dimethyl acetal in a 1.5 l sulphonation flask fitted with a stirrer, thermometer and reflux condenser. Subsequently, the pH is adjusted from about 4.5 to 1–2 with 0.5 ml of concentrated sulphuric acid and the reaction mixture is heated to reflux temperature for 3 hours at a bath temperature of 85° C. Thereafter, the mixture is cooled to room temperature and the pH value is adjusted to 7–8 with 3 ml of 30% sodium methylate in methanol. The solvent (methanol with a small amount of acetone) is distilled off over a 50 cm packed column (Θ 2.5 cm) filled with Wilson coils at normal pressure, a head temperature of 62°–65° C. and an oil-bath temperature of 90°–95° C. and the residue is subjected to a fractional distillation under reduced pressure (water-jet vacuum) over a silver-coated 10 cm packed column (Θ 1.5 cm) filled with Wilson coils). The following fractions are withdrawn:

| Fraction | Bath temperature °C. | B.p., °C. | Pressure mbar | Weight | GC area % product |
| --- | --- | --- | --- | --- | --- |
| 1 | 55° | 42–27° | $10^3$–60 | 30.0 g | 0.0 |
| 2 | 55–72° | 25–62° | 19 | 0.5 g | 3.6 |
| 3 | 69–135° | 63–65° | 19 | 41.8 g | 97.6 |
| Residue | | | | 11.3 g | |

The main fraction (3) gives 4.18 g (71.4% of the theoretical yield) of colourless liquid, b.p. 63°–65° C./19 mbar, which consists to 97.6 area % of the desired product, 2-hydroxy-2-methyl-3-butenal dimethyl acetal, according to gas chromatography.

EXAMPLE 8

Production of 2-acetoxy-2-methyl-3-butenal dimethyl acetal (Formula VII)

1.224 kg (12 mol) of acetic anhydride in a 2 l four-necked flask fitted with a reflux condenser, septum (for sample with-drawal), dropping funnel and thermometer are heated to vigorous boiling using an oil bath. Then 441.3 g (3 mol) of 2-hydroxy-2-methyl-3-butenal dimethyl acetal are added within one hour. In so doing, the bath temperature is held at 200°–215° C., so that the flask contents boil vigorously and the temperature at the head of the reflux condenser remains at about 130° C.

About 6 hours after completion of the addition of the dimethyl acetal, during which about 450 g of acetic acid-acetic anhydride have been removed, the temperature at the head of the reflux condenser increases. A further 210 g of distillate (mainly acetic anhydride) are removed.

The flask contents (about 1 kg) are now flat distilled at a bath temperature of 70°–100° C., which gives about 997 g of distillate, b.p. 48°–85° C./20 mbar (7–8 g of residue). The remaining acetic anhydride excess is then distilled off at 17–23 mbar from the distillate over a column filled with Rashig rings at a bath temperature of 90°–115° C., which gives 440–442 g of distillate consisting of practically pure acetic anhydride. The slightly yellowish coloured residue (about 550–555 g) contains only about 0.5% acetic anhydride and can be used directly for the subsequent rearrangement. It consists mainly (approximately to 97%) of the desired 2-acetoxy-2-methyl-3-butenal dimethyl acetal, b.p. 85°–86° C./20 mbar. The yield amounts to about 95% of theory.

EXAMPLE 9

Production of 7-acetoxytiglic aldehyde dimethyl acetal (Formula VIII)

A mixture of 30 g of 2-acetoxy-2-methyl-3-butenal dimethyl acetal and 0.22 g of bis-(acetonitrile)-palladium chloride is heated at 50° C. for 1 hour while stirring with a magnetic stirrer in a 50 ml round flask which is fitted with a reflux condenser and a calcium chloride tube. The palladium complex passes into solution, which is initially yellow and which becomes brown-red in colour at the end of the reaction. The flask is cooled to room temperature and the catalyst is separated using a thin-layer evaporator (jacket temperature 50° C., pressure 0.01 Torr). The product obtained (29.8 g) consists to 89.6% of trans-γ-acetoxytiglic aldehyde dimethyl acetal and to 8.7% of the corresponding cis-compound.

EXAMPLE 10

Manufacture of γ-acetoxytiglic aldehyde (Formula I)

200 ml of 1N hydrochloric acid are placed in a 250 ml four-necked flask fitted with a magnetic stirrer, thermometer and dropping funnel. 79.6 g of γ-acetoxytiglic aldehyde dimethyl acetal (0.424 mol) are added dropwise within 5 minutes while stirring intensively. The dropping funnel is rinsed with 10 ml of methylene chloride. The solution is stirred at room temperature for a further 15 minutes. After separating the aqueous phase this is extracted with 150 ml of methylene chloride and twice with a further 70 ml of methylene chloride each time. The combined organic phases are washed with 70 ml of saturated sodium bicarbonate solution and dried with 20 g of anhydrous sodium sulphate. The solvent is evaporated off on a rotary evaporator. 61.4 g of crude γ-acetoxytiglic aldehyde are obtained.

What is claimed is:

1. A process for the manufacture of an aldehyde of the formula:

$$HC\equiv C-C(CH_3)(OH)-CHO \qquad III$$

from a pentenyn-3-ol of the formula:

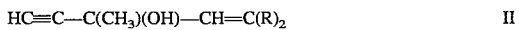

$$HC\equiv C-C(CH_3)(OH)-CH=C(R)_2 \qquad II$$

wherein R is hydrogen or methyl, comprising treating said 3-ol with ozone to form said aldehyde.

2. The process of claim 1 wherein said pentenyn-3-ol is in solution during said treatment.

3. The process of claim 2 wherein said solution contains said pentenyn-3-ol and a lower alkanol, $R^1OH$, wherein $R^1$ is $C_{1-4}$-alkyl.

4. The process of claim 3 wherein said alkanol is methanol.

5. The process of claim 3 wherein said treatment is carried out at a temperature of from about −20° C. to about 0° C.

* * * * *